(12) United States Patent
Surburg et al.

(10) Patent No.: US 8,569,383 B2
(45) Date of Patent: Oct. 29, 2013

(54) UTILIZATION OF RHINOLOGICALLY ACTIVE SUBSTANCES

(75) Inventors: Horst Surburg, Holzminden (DE); Arnold Machinek, Holzminden (DE); Hubert Loges, Hoexter (DE)

(73) Assignee: Symrise AG, Holzminden (DE)

( * ) Notice: Subject to any disclaimer, the term of this patent is extended or adjusted under 35 U.S.C. 154(b) by 772 days.

(21) Appl. No.: 12/175,156

(22) Filed: Jul. 17, 2008

(65) Prior Publication Data

US 2008/0274064 A1    Nov. 6, 2008

Related U.S. Application Data

(60) Continuation of application No. 10/626,178, filed on Jul. 24, 2003, now Pat. No. 7,414,079, which is a division of application No. 09/988,860, filed on Nov. 21, 2001, now abandoned.

(30) Foreign Application Priority Data

Nov. 24, 2000  (DE) .................................. 100 58 459

(51) Int. Cl.
*A61K 31/075* (2006.01)
*A61Q 11/00* (2006.01)
*A61K 9/00* (2006.01)

(52) U.S. Cl.
CPC ............ *A61K 31/075* (2013.01); *A61K 9/0056* (2013.01); *A61Q 11/00* (2013.01)
USPC ........... 514/715; 424/401; 424/439; 424/440; 424/48; 424/49; 424/53

(58) Field of Classification Search
None
See application file for complete search history.

(56) References Cited

U.S. PATENT DOCUMENTS

| | | | |
|---|---|---|---|
| 3,993,604 A | | 11/1976 | Thomas et al. |
| 4,130,509 A | | 12/1978 | Conrad et al. |
| 4,163,068 A | * | 7/1979 | Mussinan et al. ............ 426/538 |
| 4,476,142 A | * | 10/1984 | Netherwood et al. ............ 426/3 |
| 4,873,266 A | * | 10/1989 | Leonard et al. ............... 514/653 |
| 5,610,133 A | | 3/1997 | Monteleone et al. |
| 6,123,950 A | * | 9/2000 | Hughes ......................... 424/401 |

FOREIGN PATENT DOCUMENTS

| | | |
|---|---|---|
| EP | 262388 | 4/1988 |
| JP | 11152235 | 6/1999 |

OTHER PUBLICATIONS

Obata et al., Effect of synthesized cyclohexanol derivatives using L-menthanol as a lead compound on the percutaneous absorption of ketoprofen, Int'l J. of Pharmaceuticals, Apr. 5, 2000,198(2), pp. 191-200.
Chastrette, M. and Rallet, E. (1998), "Structure-Minty Odour Relationships: Suggestion of an Interaction Pattern," Flavour and Fragrance Journal, vol. 13, Issue 1, pp. 5-18.

* cited by examiner

*Primary Examiner* — Rosalynd Keys
(74) *Attorney, Agent, or Firm* — Duane Morris LLP; J. Rodman Steele, Jr.; Gregory M. Lefkowitz

(57) ABSTRACT

A preparation for creating a clearing feeling in a pharyngeal cavity and nasal cavity comprising a rhinologically active substance of formula (I):

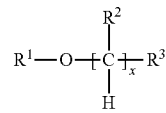

Formula (I)

In formula (I), variable x and substituents $R^1$, $R^2$ and $R^3$ have the following meanings:
x is 0 or 1,
$R^1$ denotes an alkyl group having 1 to 4 carbon atoms,
$R^2$ denotes a methyl or ethyl group, and
$R^3$ denotes a monocyclic saturated carbon system having 5, 6, 7 or 8 carbon atoms that can be unsubstituted or substituted with further alkyl groups having 1 to 4 carbon atoms or alkenyl groups having 2 to 4 carbon atoms. The compound of formula (I) can be mixed with one or more other flavor substances or aroma substances. The preparation can be an oral care composition, such as a toothpaste or a mouth wash.

17 Claims, No Drawings

UTILIZATION OF RHINOLOGICALLY ACTIVE SUBSTANCES

CROSS-REFERENCE TO RELATED APPLICATIONS

This application is a continuation of application Ser. No. 10/626,178, filed Jul. 24, 2008, which is a divisional of application Ser. No. 09/988,860, filed Nov. 21, 2001, both of which are incorporated herein by reference in their entirety.

FIELD OF THE INVENTION

The invention relates to rhinologically active substances which give rise to a refreshing and clearing feeling in the area of the mouth, the throat and the airways, and to preparations which comprise these compounds.

BACKGROUND OF THE INVENTION 1,8-Cineole (eucalyptol) is a substance which is used in large amounts as a rhinologically active substance in pharmaceutical preparations, oral care preparations, such as toothpastes and mouthwashes, and confectionery products, such as cough sweets and chewing-gum, especially because of its property of producing a cooling-refreshing and thus clearing feeling in the region of the mouth, the throat and the airways. In addition to this effect, 1,8-cineole (eucalyptol), however, has a strong typical flavor which, because of its pronounced medicinal note, is perceived as unpleasant by many consumers.

There is, therefore a requirement for substances which, in a similar manner to 1,8-cineole (eucalyptol), produce a cooling-refreshing and thus clearing feeling as a rhinologically active compound in the region of the mouth, the throat and the airways, especially in the nasal cavity, and in the pharyngeal cavity, but which do not have such a strong and unpleasant typical taste.

The advantage of such rhinologically active substances is that they are universally usable, that is to say can be used in preparations having a multiplicity of aromas of the most varying flavor notes.

Lower alkyl ethers of isobornane, here particularly of methyl isobornyl ether (Food Chem. Toxicol. 30 (Suppl.), 53S (1992), and of bornane, for example bornyl methyl ether and bornyl ethyl ether, (U.S. Pat. No. 4,131,687) have already been known for a relatively long time as fragrance and aroma substances having fresh, herb-like, rosemary-like or eucalyptus-like sensory properties. However, because of their strong typical flavor, they cannot be used as replacement products for 1,8-cineole (eucalyptol) in the sense described above.

SUMMARY OF THE INVENTION

New rhinologically active substances have been found, which are part of the formula

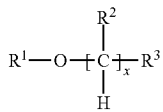

wherein
x is 0 or 1,
$R^1$ denotes an alkyl group having 1 to 4 carbon atoms,
$R^2$ denotes a methyl or ethyl group and
$R^3$ denotes a monocyclic carbon system having 5, 6, 7 or 8 carbon atoms that can be unsubstituted or substituted with further alkyl groups having 1 to 4 carbon atoms or alkenyl groups having 2 to 4 carbon atoms,

DETAILED DESCRIPTION OF THE INVENTION

The inventive new rhinologically active substances are acyclic ethers.

The alkyl group having 1 to 4 carbon atoms can be methyl, ethyl, propyl, isopropyl, butyl or isobutyl.

The alkenyl group having 2 to 4 carbon atoms can be vinyl, 2-propenyl, allyl or 2-buten-1-yl.

The radical $R^3$ can be unsubstituted or can be substituted, for example, with 1 to 3 methyl groups or with 1 isopropyl group or with 1 methyl group and 1 isopropyl group or with 1 methyl group and 1 isopropyl group or with 1 methyl group and 1,2-propenyl group.

The inventive rhinologically active substances exhibit an activity comparable to 1,8-cineole (eucalyptol) with respect to a refreshing clearing feeling in the mouth, pharyngeal cavity and the airways, without producing an unpleasant taste sensation.

These rhinologically active substances, in addition to their activity of producing a refreshing clearing feeling in the mouth, pharyngeal cavity and the airways, exhibit fresh, ethereal, minty, cooling, sweet and fruity flavor notes and are therefore also outstandingly suitable as flavor compounds.

The fact that the inventive rhinologically active compounds exhibit an activity comparable to 1,8-cineole (eucalyptol), with respect to a refreshing clearing feeling in the mouth, pharyngeal cavity and the airways, was surprising and not predictable to the extent that the inventive ethers do not have the ether linkage within the ring of a cyclic structure like 1,8-cineole (eucalyptol), but have an alicyclic structure wherein the ether linkage is not within the ring.

Preferred rhinologically active compounds in the context of the present invention are compounds of the formula

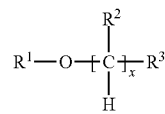

wherein
x can have the value 0 or 1,
$R^1$ denotes a methyl or ethyl group,
$R^2$ denotes a methyl or ethyl group and
$R^3$ denotes a monocyclic carbon system having 6 or 7 carbon atoms that can be unsubstituted or substituted with further alkyl groups having 1 to 3 carbon atoms and/or alkenyl groups having 3 carbon atoms.

The present flavor compounds, render pleasantly tasting flavor compounds which have the activity of causing a refreshing clearing feeling in the mouth, pharyngeal cavity and the airways. The inventive rhinologically active compounds are selected from the group of 1-menthyl methyl ether, d-menthyl methyl ether, dl-menthyl methyl ether, menthyl ethyl ether, menthyl propyl ether, menthyl isobutyl ether, isopulegyl methyl ether, 2-isopropylcyclohexyl methyl ether, 2-isopropylcyclohexyl ethyl ether, 3,3,5-trimethylcyclohexyl methyl ether, 1-(3,3-dimethylcyclohexyl)-ethyl ethyl ether, 1-(3,3-dimethylcyclohexyl)e-thyl propyl ether, and 1-(3,3-dimethylcyclohexyl)ethyl methyl ether.

The activity of causing a refreshing clearing feeling in the mouth, pharyngeal cavity and the airways, in the case of the inventive rhinologically active compounds, applies to all isomeric forms, that is to say to diastereomers and enantiomers.

The following acyclic ethers for the inventive rhinologically active compounds are novel:

Isopulegyl methyl ether, 1-(3,3-dimethylcyclohexyl)ethyl ethyl ether, 1-(3,3-dimethylcyclohexyl)ethyl propyl ether and 1-(3,3-dimethylcyclohexyl)ethyl methyl ether.

Preparation of the Ethers for the Inventive Rhinologically Active Compounds is Known per se. It can be performed, for example, by etherification of the corresponding alcohols with alkylating agents, such as alkyl halides, alkyl tosylates, alkyl mesylates or alkyl halides in the presence of an equivalent amount of a basic compound. Particularly advantageous here is etherification by the phase-transfer process, which is described, for example, in Angew. Chem. 85, 868-869 (1973), and is carried out as follows: the alcohol to be etherified is vigorously stirred in a nonpolar solvent in the presence of a phase-transfer catalyst, for example tetrabutylammonium iodide, with a 2.5-fold excess of 50% strength sodium hydroxide solution and 1.2-fold excess of an alkylating agent is added. After a customary cleanup, the corresponding ether is obtained, which is separated off from unreacted alcohol by distillation or liquid chromatography.

To achieve fresh ethereal, minty, cooling, sweet and fruity flavor notes in combination with a refreshing clearing feeling in the mouth, pharyngeal cavity and the airways, the inventive rhinologically active compounds can be combined with one another in pure form, or, in a particularly preferred form, can be combined with aroma substances or flavor substances.

Suitable aroma substances are both complex natural raw materials, such as extracts and essential oils produced from plants, and fractions and homogeneous substances produced therefrom, and also homogeneous synthetically or biotechnologically produced aroma substances.

Examples of natural raw materials are, for example:

peppermint oils, spearmint oils, Mentha arvensis oils, aniseed oils, clove oils, citrus oils, cinnamon bark oils, winter green oils, cassia oils, davana oils, spruce needle oils, eucalyptus oils, fennel oils, galbanum oils, ginger oils, camomile oils, cumin oils, rose oils, geranium oils, sage oils, yarrow oils, star anise oils, thyme oils, juniper berry oils, rosemary oils, angelica root oils, and fractions of these oils.

Examples of homogeneous aroma substances are, for example:

anethole, menthol, menthone, isomenthone, menthyl acetate, menthofuran, mint lactone, eucalyptol, limonene, eugenol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamyl isovalerate, hexanol, hexanal, cis3-hexenol, linalool, alpha-terpineol, cis and trans carvyl acetate, p-cymol, damascenon, damascone, rose oxide, dimethyl sulfide, fenchol, acetaldehyde diethyl acetal, cis-4-heptenal, isobutyraldehyde, isovaleraldehyde, cis-jasmone, anisaldehyde, methyl salicylate, myrtenyl acetate, 2-phenylethyl alcohol, 2-phenylethyl isobutyrate, 2-phenylethyl isovalerate, cinnamaldehyde, geraniol, nerol. In the case of chiral compounds, the aroma substances can be present as racemate or an individual enantiomer or as enantiomer-enriched mixture.

Examples of other flavor substances which can be advantageously combined with the inventive rhinologically active substances are, for example, substances having a physiologically cooling action, that is to say substances which cause an impression of cold in the mucous membranes. Such substances having a cooling action are, for example, l-menthol, 1-isopulegol, menthone glycerol acetal, menthyl lactate, substituted menthane-3-carboxamides (for example N-ethylmenthane-3-carbox amide), 2-isopropyl-N,2,3-trimethylbutanamide, substituted cyclohexanecarboxamides, 3-menthoxy-1,2-propanediol, 2-hydroxyethylmenthyl carbonate, 2-hydroxypropylmenthyl carbonate, N-acetylglycine menthyl ester, menthylhydroxycarboxylic esters (for example menthyl 3-hydroxybutyrate), menthyl monosuccinate, 2-mercaptocyclodecanone, menthyl 2-pyrrolidin-5-one carboxylate.

The inventive rhinologically active substances can be present in the aroma or flavor substance compositions at a content of 0.1 to 100% by weight. Preference is given to a content of 0.1 to 70% by weight; particular preference is given to a content of 0.5 to 40% by weight.

The aroma or flavor substance compositions comprising the inventive rhinologically active substances can be used in pure form, as solutions, or else in specially prepared form, and incorporated into ready-to-use products.

Suitable solvents are, for example, ethyl alcohol, 1,2-propylene glycol, triacetin, benzyl alcohol and fatty oils, for example coconut oil or sunflower seed oil.

The aroma or flavor substance compositions comprising the inventive rhinologically active substances can also comprise additives and aids, for example preservatives, pigments, antioxidants, anticaking agents, thickeners etc.

In particular prepared forms, the aroma or flavor substance compositions comprising the inventive rhinologically active substances can be bound to a carrier, spray-dried or else encapsulated.

In the bound form, the aroma or flavor substance compositions can be bound on or in a carrier, for example sodium chloride, sugar, starches or sugar melts.

The spray-dried form is produced from the liquid compositions by producing an emulsion with addition of defined amounts of a carrier, preferably biopolymers such as starch, modified starches, maltodextrin and gum arabic. This emulsion is dried in spray-dryers by very fine distribution with uniform temperature application. A powder results having the desired loading of liquid composition.

The encapsulated form is also produced from the liquid compositions by adding a carrier. Various technologies exist by which capsules can be produced. The most familiar are extrusion, spray-granulation and coazervation. The particle sizes customarily extend from 10 to 5 mm. The most familiar capsule materials are various starches, maltodextrin and gelatin. In these capsules, the liquid or solid aroma or flavor substance compositions are enclosed and can be released by various mechanisms such as use of heat, pH shift or chewing pressure.

The inventive rhinologically active substances are suitable for producing preparations of the most varied flavors, particularly for use in aroma compositions having a cooling-refreshing mint-like flavor. The mint compositions are essentially characterized by a content of peppermint oils, Mentha arvensis oils, spearmint oils, eucalyptus oils, 1,8-cineole (eucalyptol), menthol and substances having a physiologically cooling activity.

The contents of the individual composition constituents of the mint compositions can vary here generally between 0.1 and 99.9%.

Mint compositions which are preferably used are those having 1 to 90% by weight of menthol, 1 to 60% by weight of menthone, 1 to 90% by weight of peppermint or Mentha arvensis oils, 1 to 90% by weight of spearmint oils, 1 to 90% by weight of eucalyptol or eucalyptolcontaining eucalyptus oils, 0.5 to 70% by weight of the inventive rhinologically active substances, for example menthyl methyl ether, isopulegyl methyl ether or the like and 0.5 to 70% by weight of substances having a physiologically cooling action.

Mint compositions which are particularly preferably used are those having 20 to 60% by weight of menthol, 5 to 30% of menthone, 5 to 60% by weight of peppermint or Mentha arvensis oils, 5 to 60% by weight of spearmint oils, 2 to 50% by weight of eucalyptol or eucalyptol-containing eucalyptus oils, 0.5 to 40% by weight of the inventive rhinologically active substances, for example menthyl methyl ether, isopulegyl methyl ether or the like and 1 to 30% by weight of substances having a physiological cooling action.

Substances having a physiological cooling action can be the above-described, in which case they are used individually or as mixtures. If mixtures are used, these are generally mixtures, for example, of menthone glycerol acetal, menthyl lactate, substituted menthyl-3-carboxamides (for example N-ethylmenthyl-3-carboxamide), 2-hydroxyethylmenthyl carbonate and 2'-hydroxypropylmenthyl carbonate.

Generally, mixtures are used which have 1 to 99% by weight of menthone glycerol acetal, 1 to 99% by weight of menthyl lactate, 1 to 99% by weight of N-ethylmenthyl-3-carboxamide, 1 to 99% by weight of 2-hydroxyethylmenthyl carbonate and 1 to 99% by weight of hydroxypropylmenthyl carbonate.

Preference is given to mixtures having 1 to 70% by weight of menthone glycerol acetal, 1 to 70% by weight of menthyl lactate, 1 to 70% by weight of N-ethylmenthyl-3-carboxamide, 1 to 70% by weight of 2-hydroxyethylmenthyl carbonate and 1 to 70% by weight of 2-hydroxypropylmenthyl carbonate.

By adding other aroma substances, for example of the sweet, sweet-aromatic, fresh, fruity types, or if appropriate, of other flavors also, these mint compositions can be modified in flavor, with the content by weight of the added aroma substances generally being 0.001 to 50% by weight, based on the weight fraction of minty compounds and cooling compounds. Preference is given to an addition of 0.01 to 30% by weight, particularly preferably an addition of 0.1 to 10% by weight, based on the weight fraction of the minty and cooling substances.

By using the inventive rhinologically active substances in such compositions, the content of the eucalyptus oils and of 1,8-cineole (eucalyptol) and thus the strong medicinal flavor note can be reduced, without reducing the refreshing clearing feeling in the mouth, pharyngeal cavity and the airways. The perception of freshness which is produced by the inventive rhinologically active substances in the airways, in the mouth and in the pharyngeal cavity is of longer duration than that caused by 1,8-cineole (eucalyptol).

It is noteworthy, here, that the flavor intensity and roundness of flavor of the mint compositions are increased by using the inventive rhinologically active substances, and the cooling action of the substances having a physiological cooling action is intensified.

The preparations comprising the inventive rhinologically active substances can advantageously be used, especially in oral care compositions, such as toothpastes and mouthwashes, chewing-gum, foods, such as confectionery and sweets for sucking, luxury consumption merchandise, such as tobacco, pharmaceutical preparations, nasal sprays.

The content of the preparations comprising the inventive rhinologically active substances typically comprises 0.0001 to 10% by weight of rhinologically active substances. The content of the preparations comprising the inventive rhinologically active substances is, in ready-to-use mouthwashes 0.01 to 1% by weight, particularly preferably 0.1 to 0.3% by weight. In mouthwash concentrates, the content of the compositions comprising the inventive rhinologically active substances is between 0.01 and 20% by weight, preferably 0.1 to 10% by weight, particularly preferably 3 to 5% by weight. In toothpastes and chewing-gum the compositions comprising the inventive rhinologically active substances are used at a concentration between 0.1 and 5% by weight, preferably 0.5 to 2% by weight, particularly preferably between 0.8 and 1.5% by weight. In sweets for sucking, the content of the compositions comprising the inventive rhinologically active substances is between 0.01 and 2% by weight, preferably 0.05 to 1% by weight; particularly preferably between 0.1 and 0.5%.

Toothpastes that are flavored with the compositions comprising the inventive rhinologically active substances generally consist of an abrasive system (abrasives or polishes), for example silicic acids, calcium carbonates, calcium phosphates, aluminium oxides and/or hydroxyl apatites; surface-active substances, for example sodium lauryl sulphate, sodium lauryl sarcosinate and/or cocamidopropylbetaine; humectants, for example glycerol and/or sorbitol; thickeners, for example carboxymethyl cellulose, polyethylene glycols, carrageenans and/or Laponites®, sweeteners, for example saccharin; stabilizers; and active compounds, for example sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide and/or sodium bicarbonate.

Chewing-gum that is flavored with the compositions comprising the inventive rhinologically active substances generally consists of a chewing-gum base, that is to say a chewing mass which becomes plastic on chewing; sugars of various types; sugar substitutes; sweeteners; sugar alcohols; humectants; thickeners; emulsifiers; and stabilizers.

When finished products that comprise the compositions having the inventive rhinologically active substances are used, it is found that the inventive rhinologically active substances or the compositions comprising the inventive rhinologically active substances are particularly suitable for freshening the breath and neutralizing or reducing bad breath.

The use of the inventive rhinologically active substances or the compositions comprising the rhinologically active substances in oral care products, for example mouthwashes and toothpastes, and chewing-gum, leads to unpleasant, especially bitter, taste impressions being masked or neutralized, as are caused, for example, by substances such as triclosan, zinc citrate, zinc sulphate, polyphosphates and pyrophosphates, bicarbonates, strontium salts and potassium salts, tin pyrophosphate, tin chloride, aluminium lactate, hydrogen peroxide, fluorides, vitamins, cetylpyridinium chloride, and emulsifiers, for example particularly sodium lauryl sulphate, sodium lauryl sarcosinate and cocamidopropylbetaine, and sweeteners, for example aspartame, saccharin, acesulfame-K, sorbitol; xylitol, cyclamates (for example sodium cyclamate), sucralose, alitame, neotame, thaumatin, neohesperidin DC, maltitol, lactitol or chewing-gum bases.

A further positive property of the inventive rhinologically active substances which must be emphasized is their stability in toothpastes based on chalk or bicarbonate which, because of their alkaline pH, are difficult to flavor.

The inventive rhinologically active substances and the compositions comprising the inventive rhinologically active substances are also suitable, however, for use in pharmaceutical preparations, for example nasal drops and nasal sprays or embrocations. The compositions comprising the inventive rhinologically active substances are suitable, in particular, for masking the bitter taste of medicaments.

EXAMPLES

The examples below are intended to illustrate the use of the inventive rhinologically active substances. However, the use of the inventive rhinologically active substances is not restricted to the examples cited.

Example 1

Preparation of the Alkyl Ethers
General Instructions:

1 mol of the alcohol to be etherified is dissolved in 400 ml of toluene and stirred vigorously after addition of 2.6 mol, of 50% strength sodium hydroxide solution and 2 g of tetrabutylammonium iodide. At a bottom temperature of a maximum of 45° C., 1.2 mol of alkylating agent is added in the course of 1 h. The mixture is then stirred for a further 3 h at this temperature. If dialkyl sulphates were used as alkylating agent, ammonia is added to destroy them and the mixture is stirred for a further 30 min at room temperature. After addition of water, the phases are separated. The solvent is taken off from the organic phase and the residue is fractionated by distillation. The pure ethers are obtained by redistillation via a split-tube column. In this manner the following ethers were prepared:

Example 2

Production of a Toothpaste Flavoring of the Eucalyptus Menthol Type, Using Menthyl Methyl Ether The following were mixed:

0.5 parts by weight camphor
3 parts by weight anethole
6 parts by weight peppermint oil of the *Mentha arvensis* type
2 parts by weight menthyl lactate
2 parts by weight 2-hydroxyethylmenthyl carbonate
2 parts by weight 2-hydroxypropylmenthyl carbonate
20 parts by weight 1,8-cineole (eucalyptol)
64.5 parts by weight 1-menthol In a second mixture batch, the 1,8-cineole (eucalyptol) content was replaced by 1-menthyl methyl ether. Both flavorings are incorporated at a concentration of 1.3% by weight into a standard toothpaste mix based on silicic acid. Both types of toothpaste were tested under conditions of practice by an expert panel trained in sensory testing. The result showed that the flavoring containing 1-menthyl methyl ether and without 1,8-cineole (eucalyptol) markedly decreased the strongly medicinal taste, without the taste impression of freshness in the airways, mouth and pharyngeal cavity being reduced. Overall, the second flavoring led to a clearer longer-lasting taste impression with more roundness and volume.

Comparable effects are obtained if isopulegyl methyl ether, 3,3,5-trimethylcyclohexyl methyl ether or 1-(3,3-dimethylcyclohexyl)ethyl methyl ether were used instead of 1-menthyl methyl ether.

| Compound: | | | | | | Mass spectrum: | | | | | | |
|---|---|---|---|---|---|---|---|---|---|---|---|---|
| Menthyl methyl ether | m/z = | 170 | 155 | 138 | 123 | 95 | 85 | 81 | 67 | 55 | 45 | 41 |
| | % | 1 | 2 | 45 | 19 | 36 | 100 | 49 | 18 | 27 | 15 | 28 |
| Menthyl ethyl ether | m/z = | 184 | 138 | 123 | 113 | 99 | 95 | 81 | 71 | 55 | 41 | |
| | % | 2 | 36 | 12 | 8 | 100 | 20 | 26 | 28 | 18 | 20 | |
| Menthyl propyl ether | m/z | 198 | 138 | 123 | 113 | 95 | 81 | 71 | 55 | 41 | | |
| | % | 2 | 46 | 16 | 100 | 26 | 33 | 63 | 22 | 29 | | |
| Menthyl isobutyl ether | m/z | 212 | 138 | 127 | 123 | 95 | 83 | 81 | 71 | 57 | 55 | 41 |
| | % | 2 | 43 | 76 | 21 | 34 | 38 | 53 | 100 | 43 | 28 | 34 |
| 2-Isopropylcyclohexyl methyl ether | m/z | 156 | 141 | 124 | 113 | 109 | 99 | 95 | 81 | 71 | 67 | 55 | 41 |
| | % | 5 | 12 | 100 | 16 | 58 | 21 | 23 | 60 | 90 | 36 | 25 | 56 |
| 2-Isopropylcyclohexyl ethyl ether | m/z | 170 | 155 | 127 | 124 | 109 | 99 | 95 | 85 | 81 | 67 | 57 | 41 |
| | % | 8 | 16 | 24 | 100 | 55 | 18 | 20 | 96 | 50 | 26 | 75 | 38 |
| 1-(3,3-Dimethylcyclohexyl)ethyl ethyl ether | m/z | 184 | 123 | 81 | 73 | 69 | 55 | 45 | 41 | 28 | | |
| | % | 2 | 16 | 8 | 100 | 7 | 10 | 59 | 14 | 10 | | |
| 1-(3,3-Dimethylcyclohexyl)ethyl propyl ether | m/z | 198 | 183 | 123 | 87 | 81 | 69 | 55 | 45 | 41 | | |
| | % | 1 | 2 | 16 | 93 | 9 | 14 | 13 | 100 | 23 | | |
| 1-(3,3-Dimethylcyclohexyl)ethyl methyl ether | m/z | 170 | 155 | 123 | 110 | 95 | 81 | 69 | 59 | 55 | 41 | |
| | % | 1 | 3 | 13 | 5 | 6 | 9 | 7 | 100 | 10 | 12 | |
| 3,3,5-Trimethylcyclohexyl methyl ether | m/z | 156 | 141 | 124 | 109 | 99 | 85 | 67 | 58 | 55 | 41 | |
| | % | 4 | 3 | 29 | 61 | 87 | 100 | 23 | 18 | 28 | 30 | |
| Isopulegyl methyl ether | m/z | 168 | 153 | 136 | 121 | 111 | 98 | 93 | 85 | 81 | 67 | 55 | 41 |
| | % | 18 | 13 | 9 | 41 | 30 | 34 | 28 | 100 | 24 | 21 | 23 | 25 |

Example 3

Production of Toothpaste Flavoring of the Wintergreen Type Using Menthyl Methyl Ether The following were mixed:

| | |
|---|---|
| 10 parts by weight | anehtol |
| 5 parts by weight | peppermint oil of *Mentha arvensis* type |
| 5 parts by weight | peppermint oil of *Mentha piperita* type |
| 25 parts by weight | methyl salicylate |
| 40 parts by weight | 1-menthol |
| 15 parts by weight | 1-menthyl methyl ether |

The flavoring was incorporated at a concentration of 1.3% by weight into a standard toothpaste mix based on silicic acid. The toothpaste was tested under conditions of practice by an expert panel trained in sensory testing. The results showed that the flavoring gave a taste impression of high intensity and long-lasting duration, a pronounced markedly refreshing, clearing feeling being perceived in the airways, in the mouth and in the pharyngeal cavity.

Example 4

Production of a Chewing-Gum Flavoring Using 1-Menthyl Methyl Ether

The following were mixed:

| | |
|---|---|
| 40 parts by weight | peppermint oil of the *Mentha arvensis* type |
| 20 parts by weight | 1-menthone |
| 20 parts by weight | 1-menthol |
| 20 parts by weight | 1-menthyl methyl ether |

The flavoring was incorporated at a concentration of 1.5% by weight into a sugar-free standard chewing-gum base. The chewing-gum was tested for a sensory quality by a trained expert panel. It was found that addition of 1-menthyl methyl ether gave a markedly refreshing clearing feeling in the airways, in the mouth and in the pharyngeal cavity, and the taste roundness and intensity of the peppermint flavoring was markedly increased.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

We claim:

1. A preparation for creating a clearing feeling in a pharyngeal cavity and nasal cavity comprising a rhinologically active substance with formula (I):

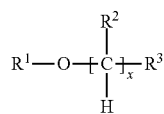

Formula (I)

wherein
x is 0 or 1,
$R^1$ denotes an alkyl group having 1 to 4 carbon atoms,
$R^2$ denotes a methyl or ethyl group, and
$R^3$ denotes a monocyclic saturated carbon system having 5, 6, 7 or 8 carbon atoms that can be unsubstituted or substituted with further alkyl groups having 1 to 4 carbon atoms or alkenyl groups having 2 to 4 carbon atoms mixed with at least one other flavor substance or aroma substance, wherein said preparation is an oral care composition selected from the group consisting of: a toothpaste and a mouth wash, wherein said at least one other flavor substance or aroma substance comprises menthane.

2. The preparation according to claim 1, wherein said rhinologically active substances are selected from the group consisting of 1-menthyl methyl ether, d-menthyl methyl ether, dl-menthyl methyl ether, menthyl ethyl ether, and mixtures thereof.

3. The preparation according to claim 1, wherein said rhinologically active substances is 1-menthyl methyl ether.

4. The preparation according to claim 1, wherein said preparation is a toothpaste having alkaline pH.

5. The preparation according to claim 1, wherein said at least one other flavor substance or aroma substance is an aroma substance selected from the group consisting of peppermint oils, spearmint oils, Mentha arvensis oils, aniseed oils, clove oils, citrus oils, cinnamon bark oils, winter green oils, cassia oils, davana oils, spruce needle oils, fennel oils, galbanum oils, ginger oils, camomile oils, cumin oils, rose oils, geranium oils, sage oils, yarrow oils, star anise oils, thyme oils, juniper berry oils, rosemary oils and angelica root oils, anethole, menthone, isomenthone, menthofuran, mint lactone, limonene, eugenol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamyl isovalerate, hexanol, hexanal, cis-3-hexenol, linalool, alpha-terpineol, cis and trans carvyl acetate, p-cymol, damascenon, damascone, rose oxide, dimethyl sulfide, fenchol, acetaldehyde diethyl acetal, cis-4-heptenal, isobutyraldehyde, isovaleraldehyde, cis-jasmone, anisaldehyde, methyl salicylate, myrtenyl acetate, 2-phenylethyl alcohol, 2-phenylethyl isobutyrate, 2-phenylethyl isovalerate, cinnamaldehyde, geraniol, nerol, and combinations thereof.

6. The preparation according to claim 1, wherein said preparation exhibits a mint-like flavor and further comprises aroma substances in an amount of 0.001 to 50% by weight, based on the weight fraction of minty compounds and cooling compounds.

7. The preparation according to claim 1, wherein said rhinologically active flavoring preparation imparts a fresh ethereal, minty, sweet and fruit flavor notes in the mouth.

8. A preparation for creating a clearing feeling in a pharyngeal cavity and nasal cavity comprising a rhinologically active substance with formula (I):

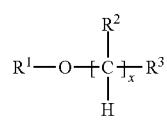

Formula (I)

wherein
x is 1 if $R^3$ denotes an unsubstituted menthyl group, and is 0 or 1 otherwise,
$R^1$ denotes an alkyl group having 1 to 4 carbon atoms,
$R^2$ denotes a methyl or ethyl group, and $R^3$ denotes a monocyclic saturated carbon system having 5, 6, 7 or 8 carbon atoms that can be unsubstituted or substituted with further alkyl groups having 1 to 4 carbon atoms or alkenyl groups having 2 to 4 carbon atoms mixed with at least one other flavor substance or aroma substance, wherein said preparation is an oral care composition selected from the group consisting of: a toothpaste and a mouth wash.

9. The preparation according to claim 8, wherein said rhinologically active substances are selected from the group consisting of isopulegyl methyl ether; 2-isopropylcyclohexyl methyl ether; 2-isopropylcyclohexyl ethyl ether; 3,3,5-trimethylcyclohexyl methyl ether; 1-(3,3-dimethyl-cyclohexyl) ethyl ethyl ether; 1-(3,3-dimethyl-cyclohexyl)ethyl propyl ether; 1-(3,3-dimethylcyclohexyl)ethyl methyl ether, and combinations thereof.

10. The preparation according to claim 8, wherein said preparation is a toothpaste having alkaline pH.

11. The preparation according to claim 8, wherein said at least one other flavor substance or aroma substance is an aroma substance selected from the group consisting of peppermint oils, spearmint oils, Mentha arvensis oils, aniseed oils, clove oils, citrus oils, cinnamon bark oils, winter green oils, cassia oils, davana oils, spruce needle oils, fennel oils, galbanum oils, ginger oils, camomile oils, cumin oils, rose oils, geranium oils, sage oils, yarrow oils, star anise oils, thyme oils, juniper berry oils, rosemary oils and angelica root oils, anethole, menthone, isomenthone, menthofuran, mint lactone, limonene, eugenol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamyl isovalerate, hexanol, hexanal, cis-3-hexenol, linalool, alpha-terpineol, cis and trans carvyl acetate, p-cymol, damascenon, damascone, rose oxide, dimethyl sulfide, fenchol, acetaldehyde diethyl acetal, cis-4-heptenal, isobutyraldehyde, isovaleraldehyde, cis-jasmone, anisaldehyde, methyl salicylate, myrtenyl acetate, 2-phenylethyl alcohol, 2-phenylethyl isobutyrate, 2-phenylethyl isovalerate, cinnamaldehyde, geraniol, nerol, and combinations thereof.

12. The preparation according to claim 8, wherein said preparation exhibits a mint-like flavor and further comprises aroma substances in an amount of 0.001 to 50% by weight, based on the weight fraction of minty compounds and cooling compounds.

13. The preparation according to claim 8, wherein said rhinologically active flavoring preparation imparts a fresh ethereal, minty, sweet and fruit flavor notes in the mouth.

14. The preparation according to claim 8, wherein x=1.

15. The preparation according to claim 8, wherein said at least one other flavor substance or aroma substance comprises menthone.

16. The preparation according to claim 1, wherein said preparation comprises 1-60 wt-% menthone.

17. The preparation according to claim 1, wherein said preparation comprises 5-30 wt-% menthone.

* * * * *